(12) United States Patent
Schlieper et al.

(10) Patent No.: US 7,911,602 B2
(45) Date of Patent: Mar. 22, 2011

(54) INSPECTION DEVICE FOR INSPECTING CONTAINER CLOSURES

(75) Inventors: Ulrich Schlieper, Rettenbach (DE); Rainer Kwirandt, Barbing (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 12/104,911

(22) Filed: Apr. 17, 2008

(65) Prior Publication Data

US 2008/0259329 A1 Oct. 23, 2008

(30) Foreign Application Priority Data

Apr. 19, 2007 (DE) .......................... 10 2007 018 870

(51) Int. Cl.
*G01N 21/00* (2006.01)
(52) U.S. Cl. ................................. 356/239.4; 356/240.1
(58) Field of Classification Search ..... 356/239.1–240.1
See application file for complete search history.

(56) References Cited

U.S. PATENT DOCUMENTS

| | | | |
|---|---|---|---|
| 4,924,107 A | 5/1990 | Tucker | |
| 5,805,279 A | 9/1998 | Palombo et al. | |
| 5,923,419 A * | 7/1999 | Thomas ..................... | 356/239.4 |
| 6,025,909 A * | 2/2000 | Juvinall et al. ............. | 356/239.4 |
| 6,260,425 B1 * | 7/2001 | Eder ............................ | 73/865.8 |
| 6,384,421 B1 | 5/2002 | Gochar, Jr. | |
| 6,643,009 B2 | 11/2003 | Takakusaki et al. | |
| 6,689,978 B2 | 2/2004 | Gresko et al. | |
| 7,010,863 B1 * | 3/2006 | Juvinall et al. ............. | 33/522 |
| 7,209,575 B2 | 4/2007 | Spaeth | |
| 7,417,725 B2 * | 8/2008 | Colle et al. .................. | 356/240.1 |

FOREIGN PATENT DOCUMENTS

| | | |
|---|---|---|
| DE | 198 52 369 C1 | 3/2000 |
| DE | 101 46 449 A1 | 4/2003 |
| DE | 102 35 658 A1 | 2/2004 |
| EP | 0 370 570 A1 | 5/1990 |
| EP | 1 270 433 A2 | 1/2003 |
| EP | 1826 556 A2 | 8/2007 |
| GB | 2 173 299 A | 3/1986 |
| JP | 60201241 A | 10/1985 |
| JP | 2002267611 A | 9/2002 |
| JP | 2002286435 A | 10/2002 |
| WO | WO-2009044574 A1 | 4/2009 |

* cited by examiner

*Primary Examiner* — Michael P Stafira
(74) *Attorney, Agent, or Firm* — Marshall, Gerstein & Borun LLP

(57) ABSTRACT

An inspection device (1) for inspecting container closures (10), having an illumination device (4) which is situated above the container closures (10) to be inspected and illuminates the container closures, an image recording device (2) which is situated above the container closures (10) to be inspected and which records the radiation directed from the illumination device (4) onto the container closures (10) and reflected back by the container closures (10) and outputs a locally resolved image of the container closures. The distance between the image recording device (2) and the container closure (10) to be inspected is less than ten times the height of the container closure (10), and the image recording device (2) has a lens (8) which has a focal length of less than 10 mm.

14 Claims, 4 Drawing Sheets

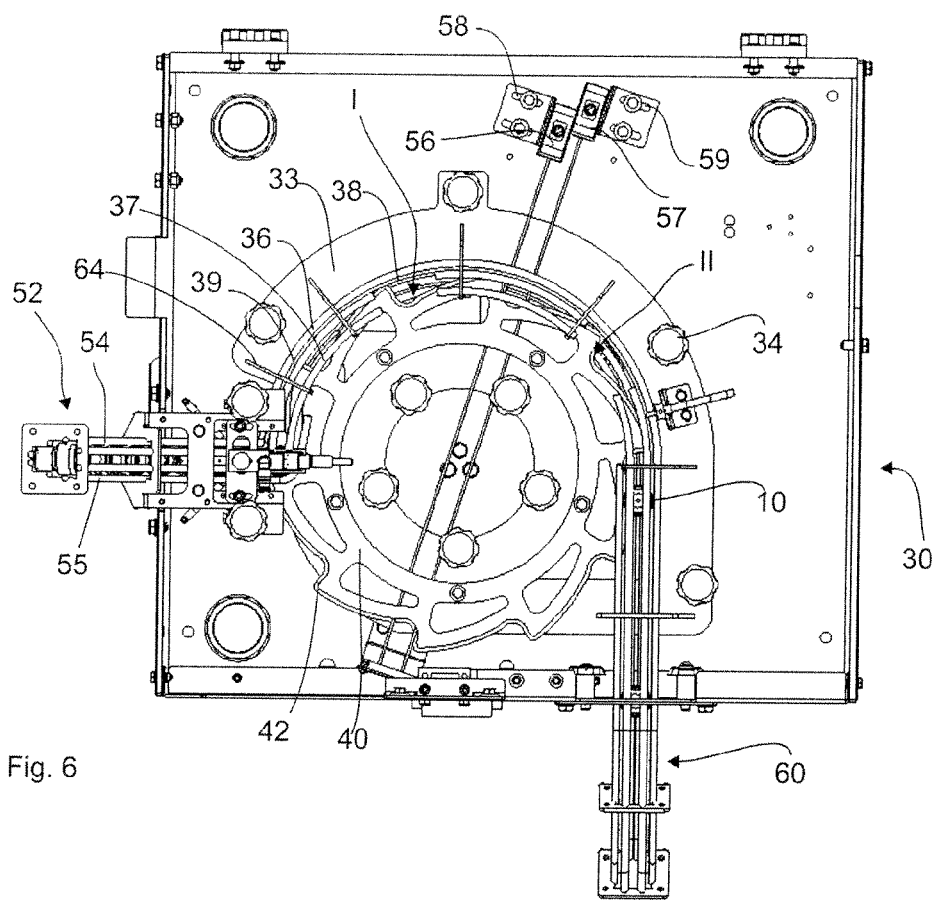

INSPECTION DEVICE FOR INSPECTING CONTAINER CLOSURES

CROSS-REFERENCE TO RELATED APPLICATION

The present application claims the benefit of German Patent Application No. 10 2007 018 870.8 filed on Apr. 19, 2007. The entire text of the priority application is incorporated herein by reference in its entirety.

FIELD OF THE DISCLOSURE

The present disclosure relates to an inspection device for inspecting container closures, such as used in beverage bottling operations.

BACKGROUND

Various devices for inspecting containers are known from the state of the art, especially in the field of the beverage industry. These devices inspect the outside wall or the mouth of the containers, for example, for defects. However, it is also necessary to inspect not only the containers themselves but also their closures for defects. For example, it is possible for such container closures to have a cross section that deviates from a certain target cross section, e.g., a circular cross section. It is also possible that a securing ring which is usually provided on such containers might be damaged.

However, inspection of container closures is associated with a number of problems. First, the container closures have a wide variety of colors, ranging from white to colors such as red, green or even black. This makes an optical inspection difficult because the corresponding container closures reflect light in different intensities. In addition, on the inside, such container closures often have protective films, e.g., made of aluminum, which strongly reflect light and thus make observation difficult.

U.S. Pat. No. 4,924,107 describes such a device for inspecting the inside surfaces of a container. This device has a camera, which observes the inside surface of a container. In addition, an illumination means is also provided for illuminating the interior space of the object.

This device operates satisfactorily for containers but it is not suitable for container closures of different colors because the reflection that occurs in observation cannot be adequately suppressed.

DE 19 852 369 C1 describes a device and a method for testing cylindrical test objects. In this method, a light is passed through the objects to be inspected and a transmission image of the test objects is recorded with the help of a camera. However, this device is not suitable for objects that are not transparent, such as the nontransparent container closures to be inspected.

SUMMARY OF THE DISCLOSURE

Therefore, the object of the present disclosure is to create a device for inspecting container closures, which will allow an inspection of container closures of a wide variety of colors on the one hand, while on the other hand suppressing interfering reflections from the container closure itself or from a conveyance device for the container closures. Any defects in the container closures should be represented in a readily visible manner in the respective image to be analyzed.

In addition, an inspection of the container closures should also be achievable even with relatively high conveyance speeds of the closures and with satisfactory resolution. Finally, the cost and complexity, e.g., the number of cameras to be used, should be as low as possible.

A disclosed inspection device for inspecting containers has an illumination device which is arranged above the container closures to be inspected and illuminates the container closures. In addition, an image recording device, which records the radiation directed by the illumination device onto the container closures and reflected back by the container closures and outputs a locally resolved image of the container closures, is arranged above the container closures to be inspected. According to this disclosure, the distance between the image recording device and the respective container closure to be inspected is less than ten times the height of the container closure, and the image recording device has a lens with a focal length of less than 10 mm.

The image recording equipment includes in particular a camera and especially preferably a color camera that records a locally resolved image. In contrast with the state of the art cited above, the objects are observed in reflected light instead of transmitted light with the present disclosure. More specifically, the image of the container closure recorded as a reflected image.

According to this disclosure, the camera is set up a very short distance away from the container closure and a lens with a small focal length and/or a wide-angle lens is used for the observation. The distance between the image recoding device and the container closure to be inspected and/or its upper edge is less than eight times the height of the container closure and is especially preferably less than four times the height of the container closure. Thus, according to this disclosure, as stated, a strong wide-angle lens is used and thus the disadvantages associated with such an extreme wide-angle lens, i.e., in particular the distortion that occurs at the edges of the image, are deliberately accepted. Due to the use of this wide-angle lens combined with the very small distance from the object to be observed, however, a high light efficiency can be achieved and thus even problematical closures, in particular dark closures, can be observed satisfactorily.

In another disclosed embodiment, the distance between the container closure and the image recording device is less than 100 mm, preferably less than 80 mm, more preferably less than 50 mm and especially preferably less than 27 mm. The exact dimension of this distance, however, also depends on the geometry of the container closure.

Thus the side wall of a container closure can be inspected fully with a lens of short focal length and at a short distance. For example, a shallow incident light beam illuminates the side walls very well, but when the covers are tall, only inadequate light reaches the respective bottom of the container closure.

With greater incident beam angles the bottom of the container closure is illuminated better, but in this case there is also increased reflection.

The radiation preferably strikes the container closure at an angle greater than 10° and preferably greater than 20° with respect to the axis of symmetry of the container closure.

For illumination of the container closure, light of different colors and/or wavelengths may preferably be used. For example, a good contrast can be achieved by using green light with a green container closure. A photograph with red light on a red container closure, for example, can also supply a favorable brightness and a favorable contrast. Through the specially adapted illumination device, it is also possible to visualize any damage to the quality strip on the container closure.

However, it would also be possible to use light of any color that does not match the color of the respective container closure, e.g., red light to inspect a green container closure. With this procedure, the contrast between the container closure and the background may be altered and the image brightness may also be reduced. The reflections and in particular reflection from the edges of the container closure may appear stronger here.

In a preferred embodiment, the inspection device has a control unit which causes the image recording device to record an image of the container closure at the point in time when the container closure is situated directly beneath the image recording device.

An arrangement directly beneath the image recording device is understood to mean that an axis of symmetry of the image recording device and the axis of symmetry of the container closure are shifted in relation to one another by less than 5 mm, preferably by less than 2 mm, and especially preferably by less than 1.5 mm.

As mentioned above, a lens having a very short focal length is used for observation, and due to the use of this lens, the image is more or less greatly distorted toward its edges. For this reason, it is advantageous to record the image exactly at the moment when the container closure is situated directly beneath the image recording device.

In another advantageous embodiment, a first polarization filter device is arranged in the beam path between the illumination device and the container closure.

As mentioned above, a plurality of reflexes occur on different container closures and the guide mechanism for these container closures also reflects or scatters the light striking them under some circumstances. Such interfering reflection can be partially suppressed by using the polarization filter device.

In another advantageous embodiment, a second polarization filter device is provided in the beam path between the container closure and the image recording device. The combination of the first and second polarization filter devices, whereby the first polarization filter device is arranged in the optical beam path upstream from the container to be inspected and the second polarization filter device is arranged in the beam path downstream from the container closure to be investigated, allows interfering reflections to be suppressed in an especially advantageous manner. The second polarization filter device, i.e., the polarization filter device arranged on the image recording device is especially preferably adjustable.

However, it would also be possible for the first polarization filter device, which is preferably situated on the illumination device, to be adjustable.

In another advantageous embodiment, a (Fresnel) lens is provided in the beam path between the illumination device and the container closure. Such lenses have an extremely short focal length. Although the optical quality of such lenses is often less favorable because this lens is used only for illumination, this disadvantage is acceptable.

In a preferred embodiment, the illumination device has a plurality of light sources which are arranged in the circumferential direction around the image recording device. These light sources are especially preferably arranged above the image recording device. Due to this special arrangement, the uniform illumination of the container closure and/or its side walls from all sides is possible. The individual light sources are especially preferably arranged symmetrically with regard to the axis of the image recording device and thus also with regard to the container closure to be observed.

In another advantageous embodiment, a preferably structureless and/or homogeneous background surface is arranged beneath the container closures. This background surface allows a high-contrast image of the respective container closure to be made.

The present disclosure is also directed to an inspection arrangement for container closures, whereby this inspection arrangement has at least one inspection device of the type described above as well as a conveyance device which moves the container closures with respect to the inspection device.

The inspection arrangement advantageously has a guide rail along which the container closures are guided individually.

In another advantageous embodiment, the inspection arrangement has at least two guide carriers (also referred to below as a sawtooth ring) which are at least temporarily in contact with the different areas of the container closure. It is also possible that such a guide carrier is in contact with a first area and another guide carrier is in contact with a second higher area, for example, in order to achieve in this way the result that the fewest possible guide elements interfere with the recording of an image.

In the advantageous embodiment, the respective guide carriers are dark or black in color. Due to this coloration, it is possible to counteract the formation of unwanted reflections.

The present disclosure is also directed to an inspection arrangement for inspecting containers, whereby this inspection arrangement has an inspection device for inspecting container closures with an illumination device which is arranged above the container closures to be inspected and which illuminates the container closures. In addition, the inspection device has an image recording device arranged above the container closures to be inspected, so that the image recording device records the radiation directed by the illumination device onto the container closures and reflected back by the container closures and outputs a locally resolved image of the container closures. According to this disclosure, this inspection device has a conveyance device which moves the container closures separately with respect to the inspection device.

This inspection arrangement preferably has a rod guide, whereby no rods are arranged in the area of the inspection device above the container closures. In another advantageous embodiment, the inspection arrangement has a guide wheel which has a plurality of recession its outer circumference, the container closures to be inspected being arranged in these recesses. With these embodiments it is possible to achieve the result that the respective container closures are passed by the inspection device with a high precision and thus also an image of the container closures is recorded in the correct period of time. The inspection device is preferably embodied in the manner described above.

The present disclosure is also directed to a method for inspecting container closures, whereby container closures to be inspected are passed by and beneath an illumination device and are illuminated by the illumination device, whereby the light cast by the illumination device and the container closures and reflected back by the container closures is at least partially recorded by an image recording device arranged above the container closures, and the image recording device outputs a locally resolved image of the container closures. According to the disclosure, the minimum distance between the image recording device and the container closures is less than ten times the height of the container closures and the image recording device images the container closures by means of a lens with a focal length of less than 10 mm. The focal length of the lens is preferably less than 10 mm, more preferably less than 4 mm, and more preferably yet the distance between the container closures and the image recording device is less than 40 mm and more preferably less than 30 mm.

In an advantageous method, the image recording device records an image of the container closures at a point in time when the container closures are directly beneath the image recording device.

BRIEF DESCRIPTION OF THE DRAWINGS

Additional advantages and embodiments are derived from the accompanying drawings, in which:

FIG. 6 shows a disclosed arrangement without the device for inspecting container closures; and FIG. 7 shows a view of a detail of the device from FIG. 6.

DETAILED DESCRIPTION OF THE PREFERRED EMBODIMENT

Figure 1:
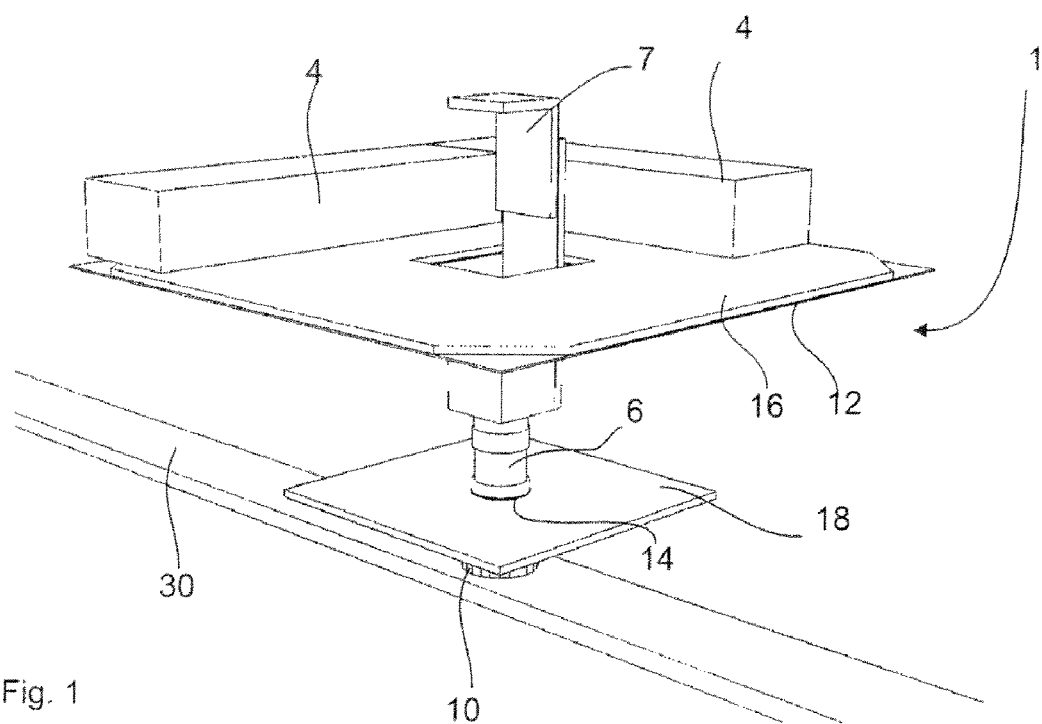
FIG. 1 shows a perspective view of a disclosed inspection device.

FIG. 1 shows a schematic diagram of an disclosed device 1 for inspecting container closures 10. These container closures are passed by the device 1 on a conveyance device 30, which is shown here only schematically.

The device 1 has several illumination devices 4, but only two illumination devices 4 are shown here. These illumination devices 4 are designed here as cube-shaped elements, which are arranged around the image recording device 2, i.e., a camera 6, in the circumferential direction. The disclosed device 1 is thus intended for the purpose of inspecting the container closures from above. A Fresnel lens 16 is arranged beneath the illumination devices 4, and a first polarization filter device 12 is in turn arranged beneath this Fresnel lens 16. This Fresnel lens 16 causes the light emitted by the illumination devices 4 to pass through a pane of glass 18 onto the container closures 10, i.e., to be diffracted strongly accordingly. Directed light, i.e., radiation directed for observation of the container closures 10, is especially preferred for use here. The light cast back, i.e., reflected by the container closure 10 is directed via a second polarization filter device 14 onto the image recording device 2. The image recording device 2 is in turn arranged on a carrier 7 and also has a lens 8 and the second polarization device 14 in addition to the camera 6.

Figure 2:
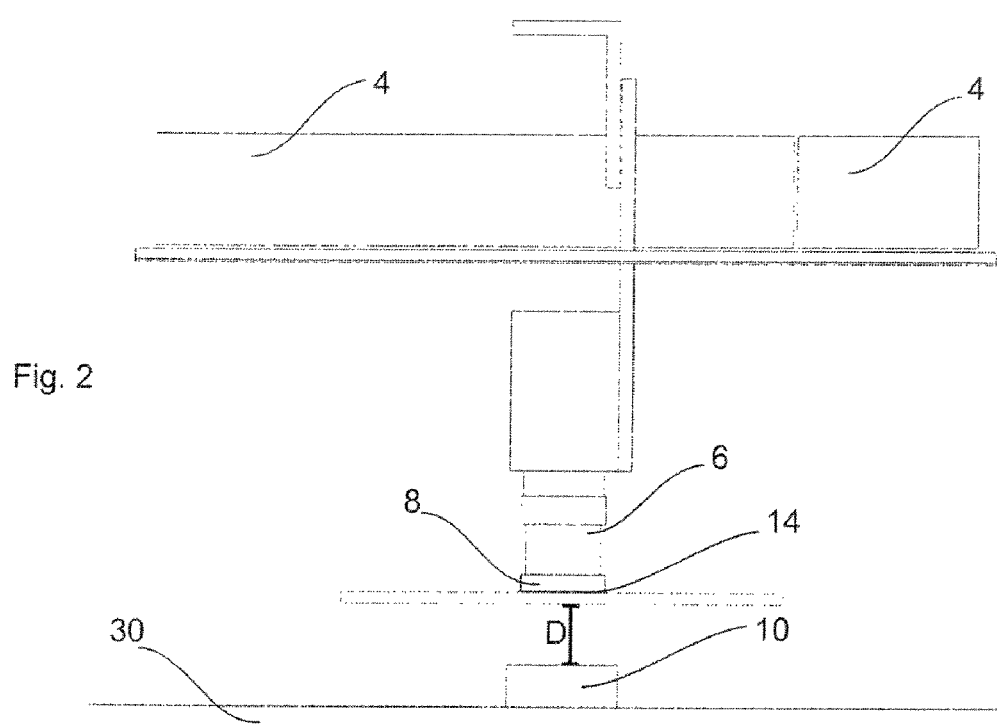
FIG. 2 shows a side view of the inspection device from FIG. 1.

FIG. 2 shows a side view of the device 1 shown in FIG. 1. The reference numeral 8 refers to a lens for an image recording device 2. This lens is a wide-angle lens, which is brought as close as possible to the container closures 10 according to this disclosure. In this way, the side walls of the container closures 10 can also be discerned well. A standard lens with a focal length of 3.5 mm is especially preferably used.

As already mentioned, reflections from the container closure 10 and guides (not shown) are to be suppressed, so polarized light is used and the light losses that might be associated with this are accepted and/or compensated with a stronger light source 4 accordingly. It should be recalled here that reflections that are not constant for each container closure and therefore should also be suppressed occur on the container closures 10.

Depending on the container closure to be inspected, the strongest possible contrast is preferably achieved between the background of observation and the container closure 10 itself. The background (not shown in FIG. 2) is preferably unstructured and monochromatic. To be able to process strong color variations, i.e., container closures 10 having different colors, this background is especially preferably interchangeable as a function of the type of product, i.e., a dark background is preferably used with container closures 10 having a light color, and a light background is especially preferably used with container closures 10 having a dark color.

For the inspection of black container closures 10 in particular, it is also necessary to minimize the outside light penetrating in from the outside, for example.

It would preferably be possible to move the container closures 10 on a conveyer belt without guide elements such as rods, for example. In this way an optimal background could be achieved. However, such a type of conveyance is possible only with wide and/or flat container closures. An inventive arrangement is shown below which combines the avoidance of excessively great reflection with the possibility of also conveying a wide variety of container closures 10.

The illumination device 4 especially preferably emits RFGB white light. As mentioned above, a color camera 6 is used to record the images. The combination of these procedures allows a wide variety of container closures 10 to be inspected, whereby the color information output by the camera 6 increases the quality of detection and allows the identification of container closures 10 of various colors.

In addition, the strongest possible illumination should be provided because the typical image resolution of 0.1 mm per pixel and the speeds, which amount to between 1 and 2 µs, require an exposure time less than 200 µs and especially preferably in the range of 100 µs. As mentioned above, a further weakening of the light occurs due to the polarization of same. The reference notation D refers to the distance between the image recording device and the container closure 10.

Figure 3:
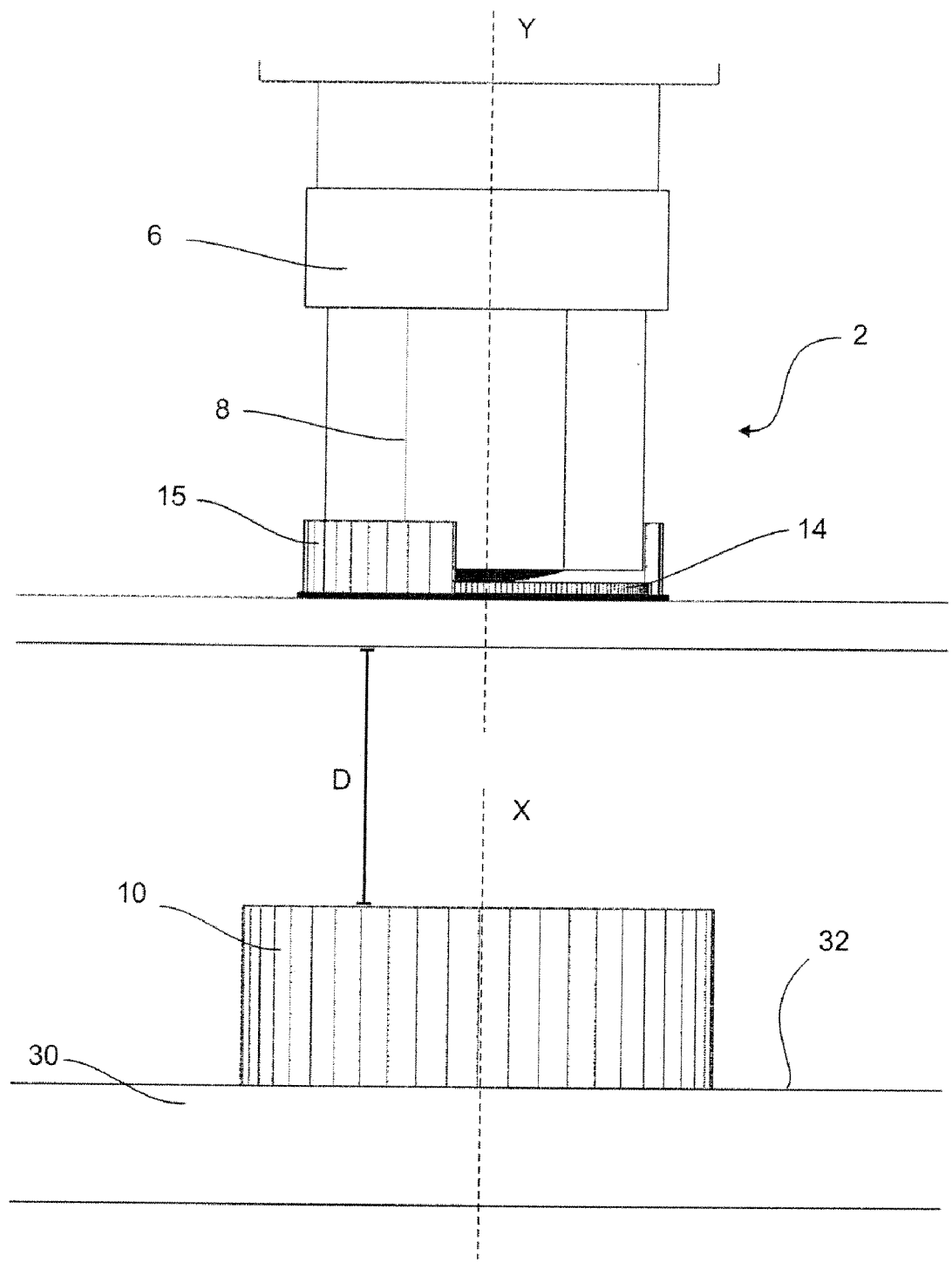
FIG. 3 shows a view of a detail of the inspection device from FIG. 1.

FIG. 3 shows a view of a detail of a disclosed inspection device 1 in which the container closure 10 is guided on a conveyer device 30 with a background 32. As soon as the container closure 10 is arranged exactly beneath the image recording device 2, an image of the container closure 10 can be made. The phrase "exactly beneath" the image recording device as used here is understood to mean that the axis of symmetry X of the container closure and the axis of symmetry Y of the image recording device 2 should essentially coincide. The reference numeral 15 refers to a rotary ring with which the polarization filter device 14 can be rotated about the axis Y to prevent reflection as much as possible. The reference numeral 8 characterizes the lens for imaging the container closure 10 on the image recording device, i.e., the camera 6.

To achieve the result that the container closure 10 is imaged at the moment in which it is directly beneath the image recording device 2, a lateral guide should preferably be provided for the container closures 10, allowing only minor tolerances. The container closures should preferably be positioned within a tolerance range of max. 2 mm and preferably 1 mm with respect to the middle position because there is great distortion in the edges due to the small distance between the image recording device 2 and the container closures 10. In addition, one should preferably also be sure that the individual container closures are spaced a sufficiently great distance apart so that the container closures 10 can be illuminated from all sides.

The image recording device 2 is provided for observation of ovality closures, warranty strip closures, sealing closures, foreign closures from above and for inspection to detect skewed positions. With the help of another image recording device (not shown) with a side view, the height of the container closure and additional caps, for example, may also be inspected. Furthermore, it would also be possible to refine the inventive inspection device by an additional image recording device.

Figure 4:
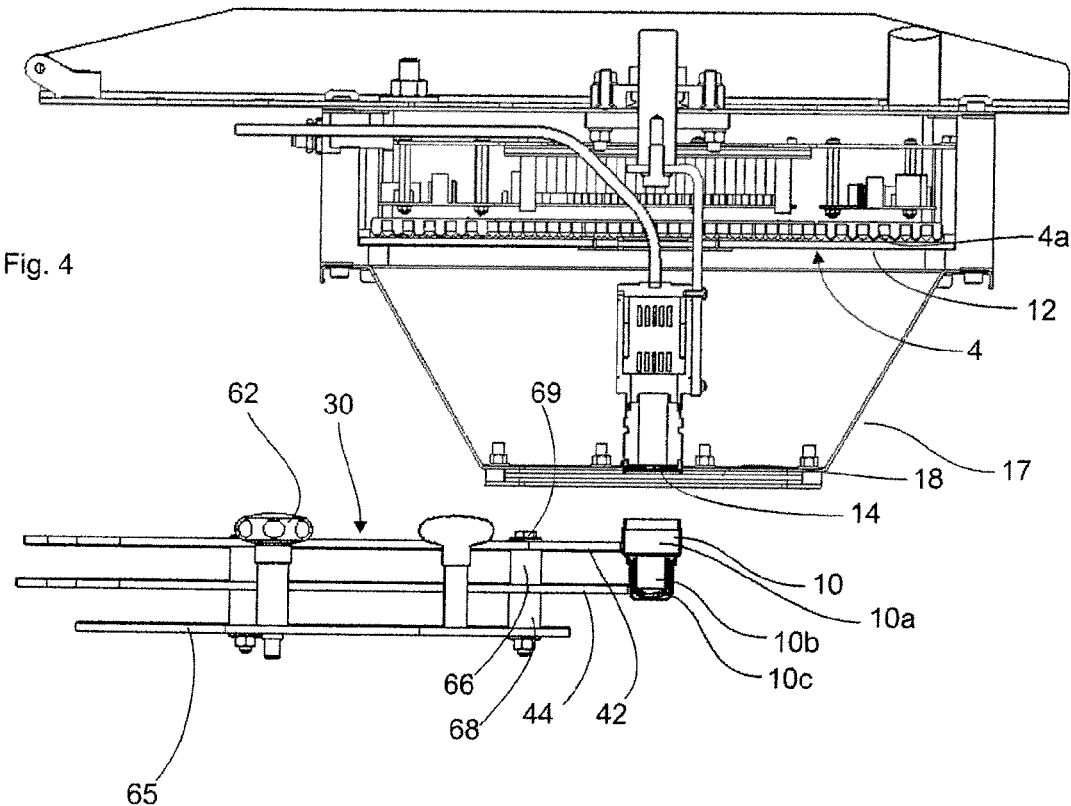
FIG. 4 shows a top view of an inventive arrangement for inspecting container closures.

FIG. 4 shows a side view of a disclosed device 1 for inspecting the container closure 10. This container closure 10 has a main body 10a in which a thread is provided for screwing it onto a container and has a cylindrical protrusion 10b over which a protective cap 10c is arranged. The disclosed device 1 for performing the inspection is arranged in its totality in a housing 17 to prevent outside light from penetrating in from the outside. The illumination device 4 has a plurality of light sources 4a in the form of LEDs. The reference numeral 16 refers here again to the Fresnel lens and the reference numeral 12 refers to the first polarization filter device. It can be seen here that the image recording device 2 is arranged centrally inside the housing 17. The pane of glass 18 serves to protect the device 1 for inspecting container closures 10.

The reference numeral 30 identifies a conveyance device by means of which the container closures 10 are supplied. This conveyance device has two guide carriers in the form of sawtooth rings 42 and 44 which are arranged parallel to one another and, as explained in greater detail below, guide the individual container closures 10. The reference numeral 65 refers to a driven star wheel which is connected to the two abovementioned sawtooth rings 42 and 44 via screw connections 69 with spacer sleeves 66 and 68. This star wheel 65 is driven and therefore the two abovementioned sawtooth rings 42 and 44 are also driven. It should be pointed out that the driven star wheel 65 is not arranged in the area in which the inspection of the container closures 10 takes place. The reference numeral 62 refers to a rotating grip for manually screwing the complete sawtooth system onto a driven wheel (not shown in FIG. 4).

Figure 5:
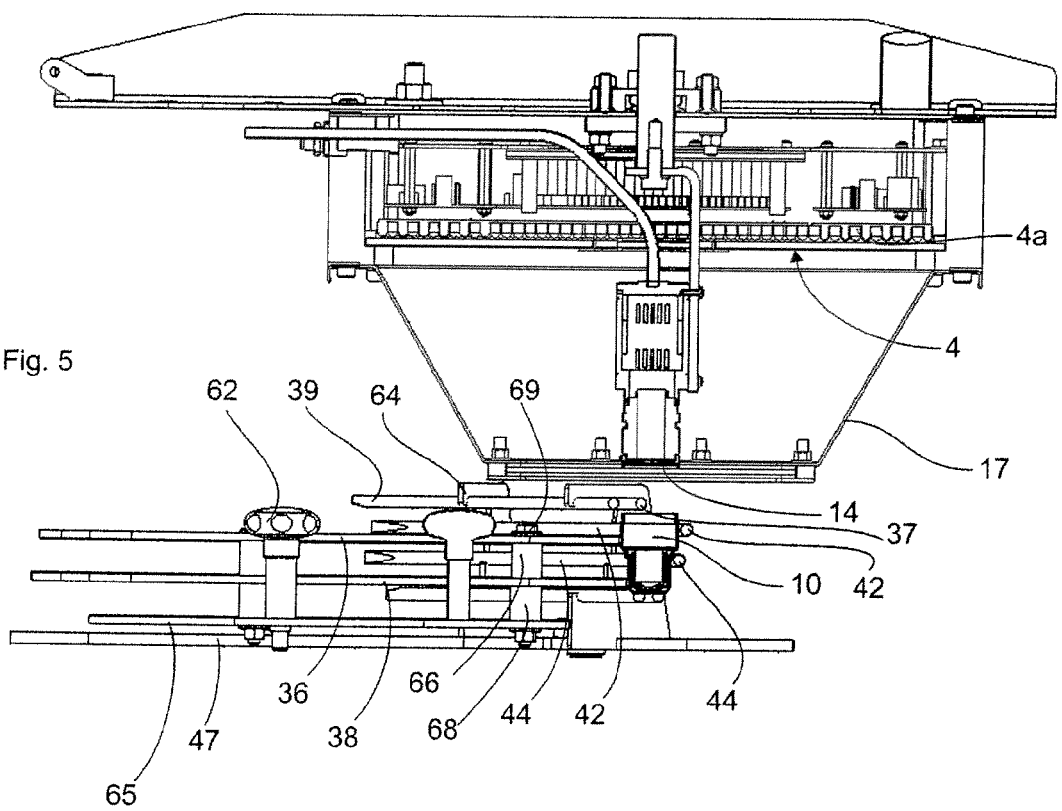
FIG. 5 shows the diagram from FIG. 4 with additional details.

FIG. 5 shows the diagram from FIG. 4 with additional details. It can be seen here that the sawtooth rings 42 and 44 are also each arranged on the right side with respect to the container closure 10. Above the container closure 10 there are two guide rods 37, 39 which serve to guide the container closures 10. These guide rods 37, 39 are held by carriers 64 running radially. It is printed out here that the guide rods 37, 39 are also not provided in the area of the actual inspection of the container closures.

The reference numerals 36 and 38 also refer to guide rods, but the lower guide rod 38 is in contact with the protrusion 10b on the container closure 10 and the upper guide rod 36 is in contact with the main body 10a of the container closure 10.

It should be pointed out that the individual sawtooth rings are interchangeable and can be released with the help of the abovementioned screw closures 69 to adapt the device to different shapes of the container closures 10. The reference numeral 47 refers to a carrying plate for the abovementioned carrier 64 which runs radially inward. This carrier plate 47 is interchangeable jointly with the carriers 64.

FIG. 6 shows a top view of an inventive conveyance device 30, whereby for the sake of better comprehensibility here, the actual inspection device 1 has been omitted. The inspection device 1 would be provided in the area labeled as 1 in which the two guide rods 37 and 39 are interrupted. The reference numeral 52 refers to a feed mechanism with which the container closures are supplied to the conveyance device 30. This feed mechanism 52 has a plurality of guide rods, only two guide rods of which are labeled with the reference numerals 54 and 55. The reference numerals 56 and 57 refer to photoelectric barrier elements which analyze the container closures to determine whether the safety cap 10 is also present. These photoelectric barrier units 56 and 57 may be displaced into elongated holes 58, 59 to thereby adapt the device to different diameters of safety caps 10c. The pane of glass 33 is replaceable with the help of detachable rotary grips 34.

The reference numeral 42 here again denotes the sawtooth ring which is rotated clockwise in FIG. 6 to convey the container closures 10. After complete inspection of the container closures, they are removed via a discharge device 60 which in turn has a plurality of guide rods. Defective container closures can be sorted out in an area 11 where they are blown away and upward, for example. To this end, the guide rods 37, 39 are also interrupted here.

FIG. 7 shows a diagram in which a few details have been removed for the sake of better illustration. It can be seen that the driven star wheel 65 is connected by the screw connections 69 to the two sawtooth rings 42 and 44. Since the two sawtooth rings 42 and 44 are arranged one above the other, only a small section of the sawtooth 44 underneath can be seen. The difference in area of these two sawtooth rings 42 and 44 results from the fact that the lower sawtooth ring 44 does not act on the base body 10a of the container closure but instead acts on the protrusion 10b. It can be seen here that the sawtooth rings have a plurality of saw teeth, whereby the saw teeth each have curvatures 42a and/or 44a which are preferably adapted to the curvature of the containers 10. In this way the container closure can be positioned very accurately with respect to the inspection device (not shown) and also with respect to the photoelectric barrier units 56, 57.

The reference numeral 70 refers to an ejection unit for sorting out defective container closures.

All the features disclosed in the patent application documents are herewith claimed as essential to the disclosure inasmuch as they are novel individually or in combination in comparison with the state of the art.

The invention claimed is:

1. Inspection device for inspecting nontransparent container closures comprising an illumination device which is situated above the nontransparent container closures to be inspected and illuminates the container closures, a color camera, which is situated above the container closures to be inspected and records the radiation directed by the illumination device onto the container closures and reflected back by the container closures and outputs a locally resolved image of the container closures, the distance between the color camera and the container closure to be inspected being less than 100 mm, the color camera having a lens having a focal length of less than 10 mm, and a Fresnel lens provided in the path of the beam between the illumination device and the container closure.

2. Inspection device according to claim 1, wherein the inspection device has a control unit which causes the color camera to record an image of the container closure at the point in time when the container closure is situated directly beneath the color camera.

3. Inspection device according to claim 1, and a first polarization filter device situated in the path of the beam between the illumination device and the container closure.

4. Inspection device according to claim 3, and a second polarization filter device provided in the path of the beam between the container closure and the color camera.

5. Inspection device according to claim 4, wherein the second polarization device is adjustable.

6. Inspection device according to claim 1, wherein the illumination device has a plurality of light sources which are arranged around the color camera in the circumferential direction.

7. Inspection arrangement with an inspection device for inspecting nontransparent container closures, comprising an illumination device which is situated above the nontransparent container closures to be inspected and illuminates the container closures, a color camera which is situated above the container closures to be inspected and records the radiation directed by the illumination device onto the container closures and reflected back by the container closures and outputs a locally resolved image of the container closures, wherein the distance between the color camera and the container closure to be inspected being less than 100mm, the color camera has a Fresnell lens having a focal length of less than 10mm, and a conveyance device which passes the container closures by the inspection device at a sufficiently great distance apart so that the container closures can be illuminated from all sides.

8. Inspection arrangement for container closures having at least one inspection device according to claim 1, and a conveyance device which moves the container closures with respect to the inspection device.

9. The inspection arrangement according to claim 8, wherein the inspection arrangement has a guide rail along which the container closures are guided individually.

10. Inspection arrangement according to claim 8, wherein the inspection arrangement has at least one guide carrier which is in contact at least temporarily with different areas of the container closure.

11. Inspection arrangement according to claim 10, wherein the guide carrier are colored black.

12. Inspection arrangement having an inspection device according to claim 1, wherein the inspection arrangement has a conveyance device which moves the container closures individually with respect to the inspection device.

13. Method for inspecting nontransparent container closures comprising passing the nontransparent container closures to be inspected by an illumination device and beneath same whereby the container closures are illuminated by the illumination device, picking up the light emitted by the illumination device that strikes the container closures and is reflected back by the container closures at least partially by a color camera situated above the container closures, the color camera outputs a locally resolved image of the container closures, setting the minimum distance between the color camera and the container closures to be less than 100mm, in the color camera which images the container closures, using a Fresnell lens which has a focal length of less than 10 mm, wherein the container closures are spaced a sufficiently great distance apart so that the container closures can be illuminated from all sides.

14. Method according to claim 12, and causing the color camera to record an image of the container closures at a point in time when the container closures are situated directly beneath the color camera.

* * * * *